United States Patent
Goto et al.

(10) Patent No.: US 9,681,848 B2
(45) Date of Patent: Jun. 20, 2017

(54) X-RAY DIAGNOSTIC SYSTEM

(75) Inventors: Yasunori Goto, Takanezawa-machi (JP); Hiroaki Sato, Nasushiobara (JP)

(73) Assignee: Toshiba Medical Systems Corporation, Otawara-shi (JP)

(*) Notice: Subject to any disclaimer, the term of this patent is extended or adjusted under 35 U.S.C. 154(b) by 18 days.

(21) Appl. No.: 13/991,457

(22) PCT Filed: Jan. 19, 2012

(86) PCT No.: PCT/JP2012/051069
§ 371 (c)(1),
(2), (4) Date: Jun. 4, 2013

(87) PCT Pub. No.: WO2012/102166
PCT Pub. Date: Aug. 2, 2012

(65) Prior Publication Data
US 2013/0259209 A1    Oct. 3, 2013

(30) Foreign Application Priority Data
Jan. 26, 2011  (JP) .................. 2011-013739

(51) Int. Cl.
*A61B 6/00* (2006.01)
*A61B 6/04* (2006.01)

(52) U.S. Cl.
CPC .......... *A61B 6/4464* (2013.01); *A61B 6/4452* (2013.01); *A61B 6/0407* (2013.01); *A61B 6/4291* (2013.01)

(58) Field of Classification Search
CPC ..... A61B 6/4441; A61B 6/045; A61B 6/4464; A61B 6/4476; A61B 6/14; A61B 6/04;
(Continued)

(56) References Cited

U.S. PATENT DOCUMENTS 5,067,145 A * 11/1991 Siczek et al. ................. 378/198
5,226,069 A    7/1993 Narita
(Continued)

FOREIGN PATENT DOCUMENTS

CN    101053522 A    10/2007
JP    4 208137    7/1992
(Continued)

OTHER PUBLICATIONS

International Search Report Issued Feb. 21, 2012 in PCT/JP12/51069 Filed Jan. 19, 2012.
(Continued)

*Primary Examiner* — Glen Kao
(74) *Attorney, Agent, or Firm* — Oblon, McClelland, Maier & Neustadt, L.L.P.

(57) ABSTRACT

An X-ray diagnostic system is provided that is capable of fitting the vertical position of the X-ray tube to each mode of photography without being affected by the height of the ceiling. The X-rays irradiated from the X-ray tube and transmitted through the subject are detected, and photographed images are captured based on the detected X-rays; the system comprises a supporting member, an arm member, and a height adjuster; the supporting member is provided on the ceiling of a room, formed in a pillar shape, and configured in such a way that the entire length is vertically extended and shortened. The arm member has a base end section connected to the lower end portion of the supporting member and a tip section on which the X-ray tube is mounted. The height adjuster adjusts the vertical position of the X-ray tube by moving the tip section of the arm member relative to the supporting member.

3 Claims, 21 Drawing Sheets

(58) Field of Classification Search
CPC ... A61B 6/0407; A61B 6/0421; A61B 6/4233; A61B 6/4435; A61B 6/4452; A61B 6/501; G01T 1/17; G01T 1/2928; G01N 30/56; B60R 22/203; B60R 2021/0006; B60R 22/24; B60R 13/0206; B60R 13/025; B60R 2013/0287; B60R 2021/0435; B60R 2022/208; B60R 2022/4816; B60R 2022/485; B60R 21/04; B60R 21/055; B60R 21/213; B60R 22/20
USPC ............................................ 378/196, 197.62
See application file for complete search history.

(56) References Cited

U.S. PATENT DOCUMENTS

| | | | |
|---|---|---|---|
| 7,182,511 B2 | 2/2007 | Boomgaarden et al. | |
| 2005/0008125 A1* | 1/2005 | Rainer | A61B 6/4464 378/197 |
| 2008/0247516 A1* | 10/2008 | Fink et al. | 378/194 |
| 2011/0069812 A1 | 3/2011 | Takahashi | |

FOREIGN PATENT DOCUMENTS

| | | |
|---|---|---|
| JP | 2000 254114 | 9/2000 |
| JP | 2004 236746 | 8/2004 |
| JP | 2005-021328 | 1/2005 |
| JP | 2006 142023 | 6/2006 |
| JP | 2008-168128 | 7/2008 |
| JP | 2009-505767 | 2/2009 |
| JP | 2011 67248 | 4/2011 |
| JP | 2011-103990 | 6/2011 |

OTHER PUBLICATIONS

Chinese Office Action issued Nov. 3, 2014, in China Patent Application 201280004361.2.
Japanese Office Action issued in Application No. 2012-008809 on Aug. 25, 2015.
Japanese Office Action issued in JP Patent Application No. 2012-008809 on Apr. 5, 2016.

* cited by examiner

X-RAY DIAGNOSTIC SYSTEM

FIELD OF THE INVENTION

Embodiments of the invention are related to an X-ray diagnostic system, wherein the X-rays irradiated from an X-ray tube and transmitted through a subject are detected, and photographed images are captured based on the detected X-rays.

BACKGROUND OF THE INVENTION

In an X-ray diagnostic system, an X-ray tube is provided on the ceiling of a room via a supporting member.

FIG. 19 shows an X-ray tube which is provided on the ceiling of a room via a supporting member. As shown in FIG. 19, the supporting member has a base section 31 and a pillar section 32. The base section 31 is installed on the ceiling C via a rail L. The pillar section 32 has an upper pillar 321, a middle pillar 322 and a bottom pillar 323, which are fitted to each other. The upper pillar 321 is mounted on the base section 31. The X-ray tube 11 is provided on the bottom pillar 323 (the lower end portion of a supporting member 30). The height of the X-ray tube 11 is adjusted by extending and contracting the pillar section 32.

Regarding radiography, there is supine full-length radiography in which a subject P is placed on a bed B, in addition to standing full length radiography of the lower extremities in which the subject P is in the standing position. For example, in supine full-length radiography, the X-ray irradiation field has to be widened by making the position of the X-ray tube as high as possible so that images of the extensive part of the subject P lying on the bed can be photographed. In addition, in standing full length radiography of the lower extremities, the position of the X-ray tube has to be as low as possible to capture the images of the heel of the subject P who is standing. In other words, it is necessary to move the X-ray tube 11 over a wide range, from the higher position to the lower position, depending on each mode of photography (supine full-length radiography or standing full length radiography of the lower extremities).

However, if the ceiling in the room is low, the position of the X-ray tube 11 provided on the ceiling via the supporting member becomes low over the entire moving range. In contrast, if the ceiling in the room is high, the position of the X-ray tube 11 provided on the ceiling via the supporting member becomes high over the entire moving range.

The need for moving the X-ray tube 11 over a wide range is now described with reference to FIG. 19 and FIG. 20.

FIG. 19 shows the state of supine full-length radiography. In supine full-length radiography, the SID (source-image distance) should be large since the X-ray irradiation field has to be wide. For this purpose, the position of the X-ray tube 11 needs to be high.

There is a case that that it is not possible to make the position of the X-ray tube 11 sufficiently high by only moving the X-ray tube 11 because the ceiling in the room is low and therefore the position of the X-ray tube 11 is low over the entire moving range. In this case, a large SID (e.g., 2 [m]) should be secured. Thus, for CR (Computed Radiography) and film, without using the bed B, an IP (Imaging Plate) and a cassette are placed on the floor, and the subject P lies on top of them, which is stressful for the subject P.

FIG. 20 shows the status of standing full length radiography of the lower extremities. As shown in FIG. 20, in standing full length radiography of the lower extremities, it is necessary to lower the position of the X-ray tube 11 in order to photograph down to the heel.

There is a case that it is not possible to make the position of the X-ray tube 11 sufficiently low by only moving the X-ray tube 11 because the ceiling in the room is high and therefore the position of the X-ray tube 11 is high over the entire moving range. In this case, the subject P can stand on the platform for photography (a step) S in order to capture images of the heel of the subject; however, it is likely that the subject P undergoing standing full length radiography of the lower extremities may have a disease in the foot; therefore, having the platform for photography as low as possible is less stressful for the subject and safer.

In order to move the X-ray tube 11 over a wide range, from a higher position to a lower position, the supporting member 30 is extended and contracted with a large stroke. Herein, the general stroke for the supporting member 30 is about 1.5 to 1.8 [m].

In order to further enlarge the stroke for the supporting member 30, for example, in the event that the supporting member 30 consists of three members, the upper pillar 321, middle pillar 322 and bottom pillar 323, each of the pillars 321 to 323 should be elongated.

However, when this supporting member 30 is provided on the ceiling and each of the pillars 321 to 323 is contracted, each of the pillars 321 to 323 is long, resulting in the lower end portion of the supporting member becoming low and the position of the X-ray tube 11 provided at the lower end portion of the supporting member 30 also becoming low. Therefore, there was a problem in that it was not possible to raise the position of the X-ray tube 11 sufficiently high, and supine full-length radiography, which requires wider X-ray irradiation field, could not be performed (see FIG. 21).

Next, in order to further enlarge the stroke of the supporting member 30, for example, the supporting member 30 should have multiple pillars, with each pillar able to be shortened. However, there was a problem; since the diameter of the upper pillar became larger, it was also heavier and the multiple pillars meant a complicated structure, causing high costs and a decline in the quality of appearance (see FIG. 22).

In addition, there is a technology in which an adaptor A is added between the ceiling C and the base section 31 to adjust the position of the X-ray tube 11 to fit to the height of the ceiling C (see FIG. 23).

Furthermore, a technology exists in which the X-ray tube 11 is installed in a position at a different height relative to the supporting member 30 when installing the X-ray diagnostic system on the ceiling (e.g. patent document No. 1).

PRIOR ART DOCUMENTS

Patent Documents

[Patent document No. 1] Japanese published unexamined application No. 2004-236746

SUMMARY OF THE INVENTION

Problem to be Solved by the Invention

The above-mentioned problems existed in the technology in which each member of the supporting member 30 is elongated to secure a large stroke (see FIG. 21), as well as in the technology in which the number of members is increased in the supporting member 30 (see FIG. 22).

Also, in the conventional technology in which an adaptor A is added between the ceiling C and rail L to adjust the position of the X-ray tube 11 to fit the height of the ceiling C (see FIG. 23), there was a problem in that it was only effective when the ceiling C was high, and could not be used when the ceiling C was low.

In addition, the technology described in the above patent document in which the X-ray tube 11 is installed in a position at a different height relative to the supporting member 30 is used when installing the system on the ceiling; therefore, there was a problem in that it could not be used once the system was installed on the ceiling.

That is, when installing the system on the ceiling, in order to adjust the position of the X-ray tube 11 to fit to the height of the ceiling, the X-ray tube 11 is installed at a lower position relative to the supporting member 30 when the ceiling C is high as shown in FIG. 24, and the X-ray tube 11 is installed at the higher position relative to the supporting member 30 when the ceiling C is low as shown in FIG. 25. However, when standing full length radiography of the lower extremities is performed after installing the X-ray tube 11 at the higher position for low ceilings, the position of the X-ray tube 11 could not be sufficiently lowered to the position of the subject's heel. Also, when supine full-length radiography is performed after installing the X-ray tube 11 at the lower position for high ceilings, there was a problem in that the position of the X-ray tube 11 could not be sufficiently raised to widen the irradiation field of X-rays.

This embodiment is intended to resolve the above described problems, with the aim of providing an X-ray diagnostic system capable of fitting the vertical position of the X-ray tube to each mode of photography without being affected by the height of the ceiling.

Means of Solving the Problems

To resolve the above described problems, in an X-ray diagnostic system according to the embodiments, the X-rays irradiated from the X-ray tube and transmitted through the subject are detected, and photographed images are captured based on the detected X-rays; the system comprises a supporting member, an arm member, and a height adjuster; the supporting member is provided in a part of the room; the arm member has a base end section connected to the supporting member and a tip section on which the X-ray tube is mounted. The height adjuster adjusts the vertical position of the X-ray tube by moving the tip section of the arm member relative to the supporting member.

DETAILED DESCRIPTION OF THE INVENTION

Next, embodiments of the X-ray diagnostic system are described based on each figure.

First Embodiment

Figure 1:
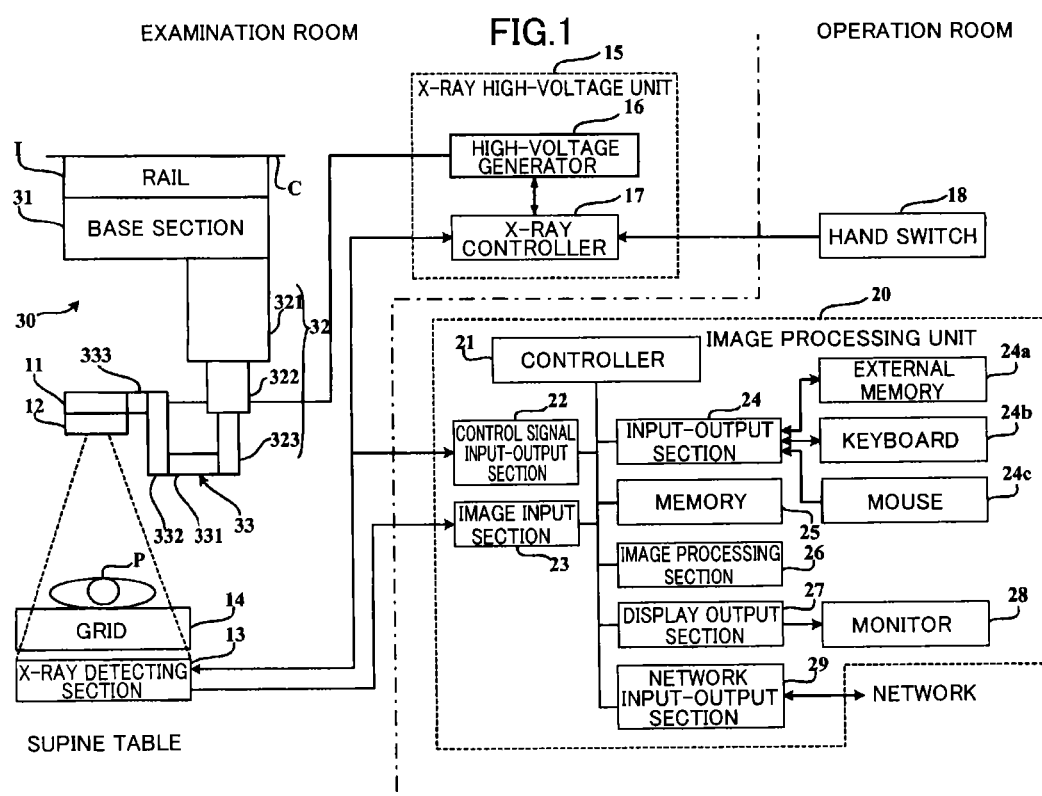
FIG. 1 is a functional block diagram of the X-ray diagnostic system according to the first embodiment.

First, the basic configuration of the X-ray diagnostic system according to the first embodiment is described with reference to FIGS. 1 through 8. FIG. 1 is a functional block diagram of the X-ray diagnostic system. Here, a drive controller 50 is omitted from being shown in FIG. 1.

The X-ray diagnostic system, as shown in FIG. 1, comprises an X-ray tube 11 for irradiating X-rays, a diaphragm 12 for determining the range of radiation of the X-rays, an X-ray detecting section 13 for detecting the transmitted X-rays, a grid 14 for removing the scattered X-rays from the transmitted X-rays, an X-ray high-voltage unit 15, and a hand switch 18.

The X-ray high-voltage unit 15 has a high-voltage generator 16 for supplying high voltage to the X-ray tube 11, and an X-ray controller 17 for receiving the signals in response to the radiography (including X-ray radioscopy) through the operation of the hand switch 18 and giving instructions to generate the predetermined voltage.

An image processing unit 20 comprises a controller 21, a control signal input-output section 22 for inputting and outputting control signals from the controller 21 for the X-rays detecting section 13; an image input section 23 wherein the transmitted X-rays detected by the X-ray detecting section 13 are converted to electric signals and the created images are input; an image processing section 26 for creating photographed images (including perspective images) from the input images; a memory 25 for storing data pertaining to the patients and radiography as well as the photographed images; a display output section 27 for displaying the photographed images on a monitor 28; an input-output section 24 for outputting the photographed images to an external memory 24a and also for inputting signals through the operation of a keyboard 24b and mouse 24c; and a network input-output section 29 for inputting and outputting the photographed images for the network.

[Supporting Member]

A supporting member 30 is provided in a rail L below the ceiling C. The ceiling C is an example of "a part of the room" in this invention. The supporting member 30 has a base section 31 and a pillar section 32. The base section 31 is installed on the ceiling C via the rail L. The pillar section 32 has an upper pillar 321, a middle pillar 322, and a bottom pillar 323. The upper pillar 321, middle pillar 322, and bottom pillar 323 are fitted so that they move with each other vertically. Thereby, the pillar section 32 is vertically telescopic.

An extension/contraction mechanism is provided for adjusting the vertical position of the X-ray tube 11 by vertically extending and contracting the pillar section 32. The extension/contraction mechanism is configured to maintain each pillar at each position by applying a predetermined force on each of the upper pillar 321, middle pillar 322, and bottom pillar 323, and to extend and contract the pillar section 32 by releasing the predetermined force applied on each pillar. The adjustment of the vertical position of the X-ray tube 11 by extending and contracting the pillar section 32 is described in detail later.

[Arm Member]

The arm member 33 is provided on the bottom pillar 323 of the pillar section 32. The arm member 33 has a base end section 331, a middle section 332, and a tip section 333. The base end section 331 of the arm member 33 is fixed to the bottom pillar 323 of the pillar section 32. The middle section 332 of the arm member 33 is fixed to the base end section 331. The tip section 333 of the arm member 33 is provided such that it is vertically movable relative to the middle section 332. The X-ray tube 11 and diaphragm 12 are provided on the tip section 333 of the arm member 33. Also, an angle adjuster (not shown) is provided to change the irradiation direction of the X-ray tube and obtain the desired angle by rotating the X-ray tube 11 and diaphragm 12 about a horizontal axis. The angle adjuster is described in detail in the second embodiment.

[Height Adjuster]

Figure 2:
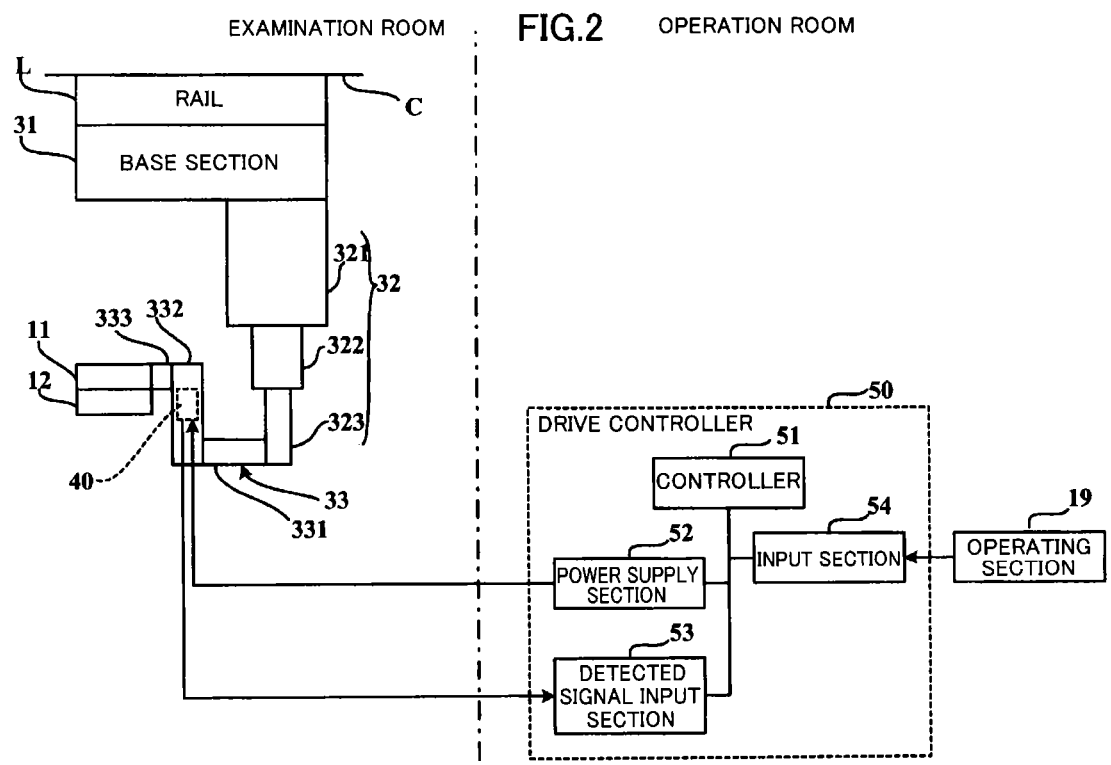
FIG. 2 is a functional block diagram of the apparatus for drive-controlling the height adjustment section.

As shown in FIG. 2, a height adjuster 40 is provided in the middle section 332.

Figure 3:
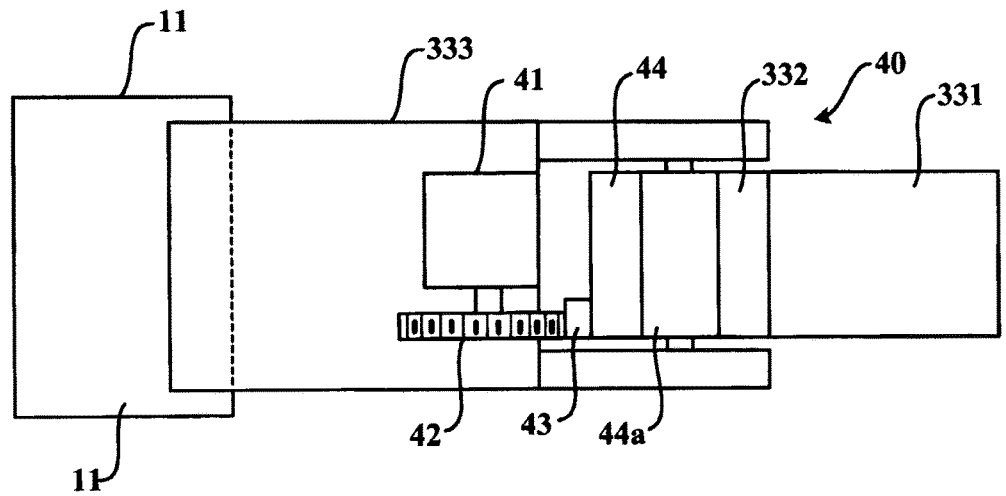
FIG. 3 is a plane view of the height adjuster.
Figure 4:
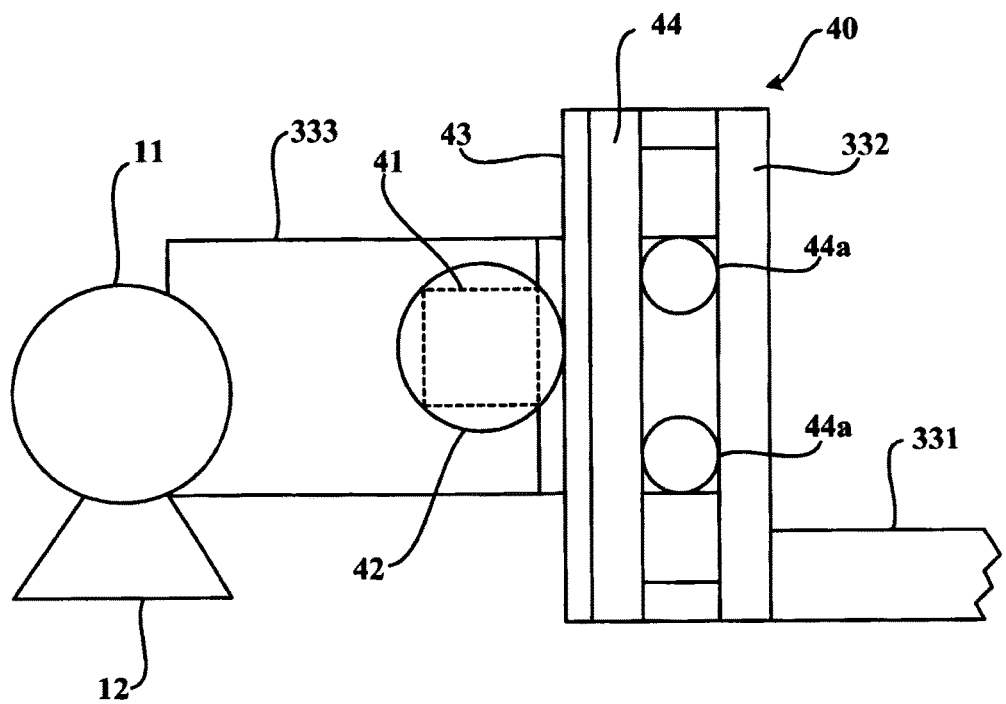
FIG. 4 is a front view of the height adjuster.

Next, the height adjuster 40 for adjusting the vertical position of the X-ray tube 11 is described with reference to FIG. 2, FIG. 3, and FIG. 4. FIG. 3 is a plane view of the height adjuster 40, while FIG. 4 is a front view of the height adjuster 40.

The height adjuster 40 is provided in the arm member 33. The height adjuster 40 is an example of the "height adjuster" of this invention. The height adjuster 40 has a sliding mechanism for adjusting the vertical position of the X-ray tube 11 by vertically moving the tip section 333 of the arm member 33 relative to the middle section 332.

The height adjuster 40 comprises a motor 41 provided on the tip section 333 of the arm member 33; a pinion 42 fixed to the output axis of the motor 41; a rack 43 provided on the middle section 332 of the arm member 33 and engaged with the pinion 42; a guiderail 44 for fixing the rack 43; and a roller 44a vertically rolling along the guiderail 44. By pinching the roller 44a with the guiderail 44, it is held in such a way that non-vertical movement of the tip section 333 of the arm member 33 is limited. As an alternative to the roller 44a and guiderail 44, a sliding guide can be used.

Since the pinion 42 is engaged with the rack 43, when rotation of the motor 41 is stopped, the tip section 333 of the arm member 33 and the X-ray tube 11 are held in predetermined vertical positions by a self-locking function such as a worm gear. Also, as alternatives for the pinion 42 and rack 43, a chain sprocket, ball screw, or lead screw can be used.

The moving direction of the tip section 333 of the arm member 33 and the X-ray tube 11 corresponds to the rotation direction of the pinion 42; for example, when the rotation direction of the pinion 42 is clockwise in FIG. 4, they move upward, while when the rotation direction of the pinion 42 is counterclockwise in FIG. 4, they move downward. The moving distance of the tip section 333 of the arm member 33 and the X-ray tube 11 corresponds to the rotation angle of the pinion 42 such that the larger the rotation angle, the longer the moving distance.

[Drive Controller]

Next, the drive controller of the height adjuster 40 is described with reference to FIG. 2. FIG. 2 is a functional block diagram of the drive controller. Here, the image processing unit 20 is omitted from being shown in FIG. 2.

The drive controller 50 is provided in the operation room and comprises a controller 51, a power supply section 52, a detected signal input section 53, and an input section 54. An operating section 19 is provided on the console panel. When the signals through the operation of the operating section 19 are transmitted to the input section 54, the controller 51 receives the signals and outputs control signals to the power supply section 52. The power supply section 52 receives the control signals and supplies the predetermined electric power to the motor 41 of the height adjuster 40. The detected signal input section 53 detects the rotation amount of the motor 41 and inputs this amount to the controller 51. The controller 51 determines whether or not the input rotation amount of the motor 41 is the rotation amount corresponding to the control signals.

Various types of motors can be used for the motor 41. For example, as an example of a motor 41, a pulse-driven servomotor is used. As an alternative for the servomotor, an induction motor and a separately attached sensor (a potentiometer and encoder) can be used.

The controller 51 receives signals through the operation of the operating section 19, generates control signals for moving the X-ray tube 11 upward or downward, and transmits the generated control signals to the power supply section 52. The power supply section 52 receives the control signals from the controller 51 and transmits the pulses with the width and number corresponding to the control signals (pulses with constant frequency) to the motor 41. The motor 41 rotates in the forward direction when the pulse width is larger than the reference width, rotating the pinion 42 at the rotation amount corresponding to the pulse width. Also, the motor 41 rotates in the reverse direction when the pulse width transmitted from the power supply section 52 is smaller than the reference width, rotating the pinion 42 at the rotation amount corresponding to the pulse width. Thereby, the motor 41 moves the tip section 333 of the arm member 33 and the X-ray tube 11 to the predetermined vertical positions. In addition, when the motor 41 is stopped, the tip section 333 of the arm member 33 and the X-ray tube 11 are maintained in the determined vertical positions by the retention force of the motor 41.

[Operation]

Next, the operation when adjusting the vertical position of the X-ray tube is described with reference to FIG. 5 to FIG. 8. FIGS. 5 to 8 are views describing the operation of the pillar section 32 and the height adjuster 40.

It is possible to fit the vertical position of the X-ray tube 11 to supine full-length radiography and standing full length radiography without being affected by the height of the ceiling C by extending and contracting the pillar section 32, and by operating the height adjuster 40.

In the extending/contracting operation of the pillar section 32 and in the operation of the height adjuster 40, either operation can be performed first, both operations can be performed alternately, or either one of the operations can be performed.

The following description describes an instance in which the pillar section 32 is extended and contracted first, and then the height adjuster 40 is operated.

Figure 5:
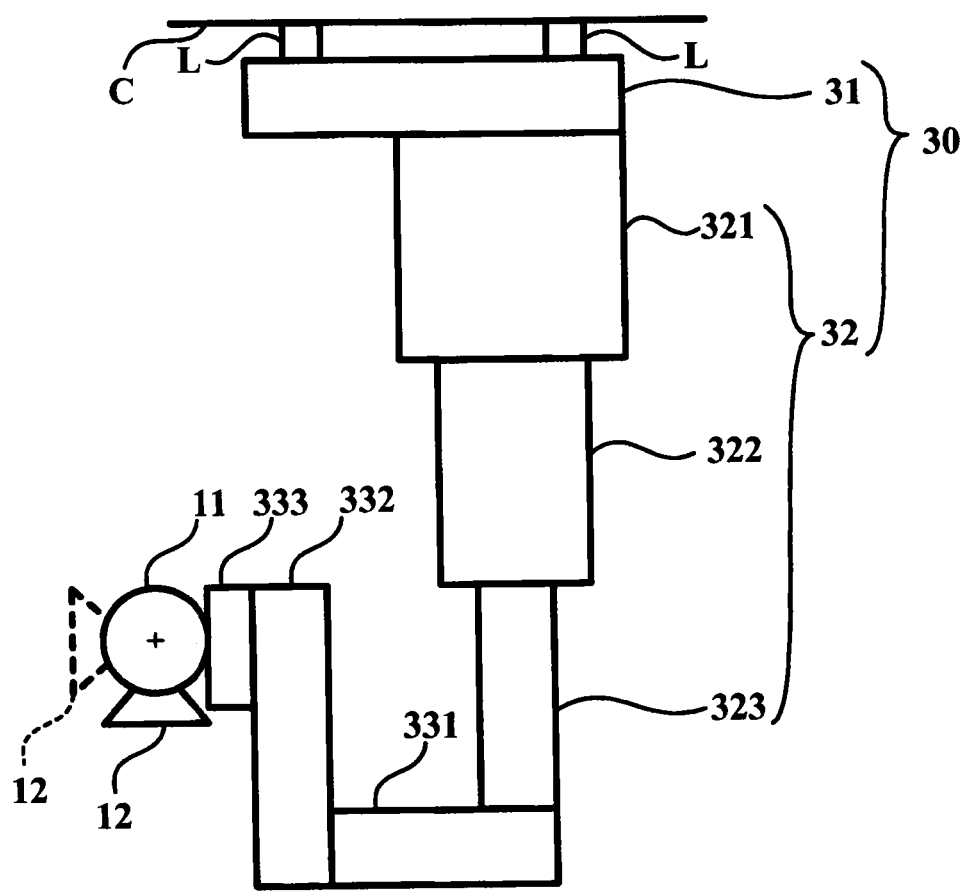
FIG. 5 is a view describing the operation of the pillar section and the height adjuster.
Figure 6:
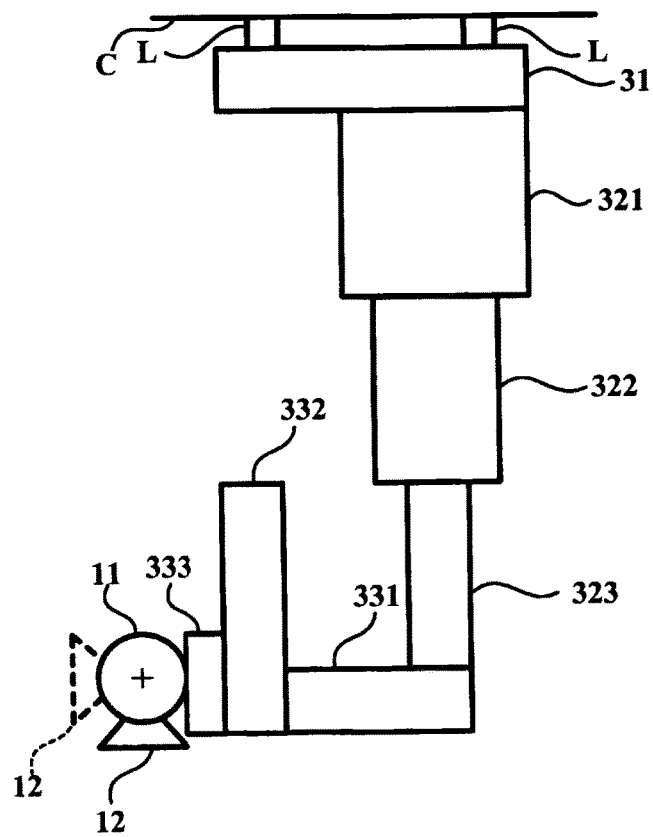
FIG. 6 is a view describing the operation of the pillar section and the height adjuster.

FIGS. 5 and 6 show the supporting member 30 installed in a rail L below the high ceiling C. As shown in FIGS. 5 and 6, by extending the pillar section 32 to move the bottom pillar 323 to the lower position, the position of the X-ray tube 11 installed on the bottom pillar 323 is lowered. Thereby, the X-ray tube 11 is held in the lower position.

Next, the height adjuster 40 is operated. The vertical position of the tip section 333 of the arm member 33 and the X-ray tube are raised by rotating the motor 41 in a clockwise direction at a predetermined rotation angle. The X-ray tube 11 which is adjusted to the highest position relative to the middle section 332 of the arm member 33 is shown in FIG. 5.

Also, the vertical position of the tip section 333 of the arm member 33 and the X-ray tube are lowered by rotating the motor 41 counterclockwise at a predetermined rotation angle. The X-ray tube 11, which is adjusted to the lowest position relative to the middle section 332 of the arm member 33, is shown in FIG. 6.

As described above, even in the event that the ceiling C is high, by extending the pillar section 32 and adjusting the X-ray tube 11 to its lowest position (see FIG. 6) enough to lower the position of the X-ray tube 11, it is possible to address the standing full length radiography of the lower extremities in which the subject is standing while the heels are photographed.

Figure 7:
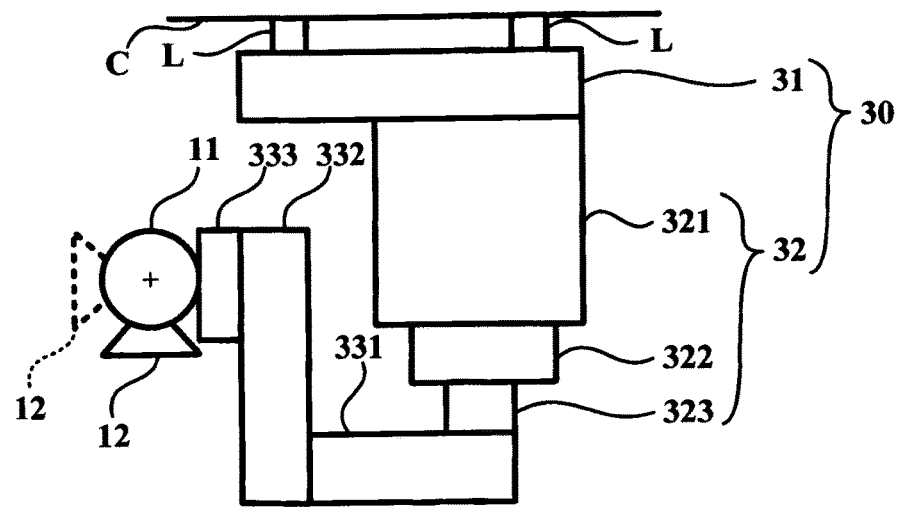
FIG. 7 is a view describing the operation of the pillar section and the height adjuster.
Figure 8:
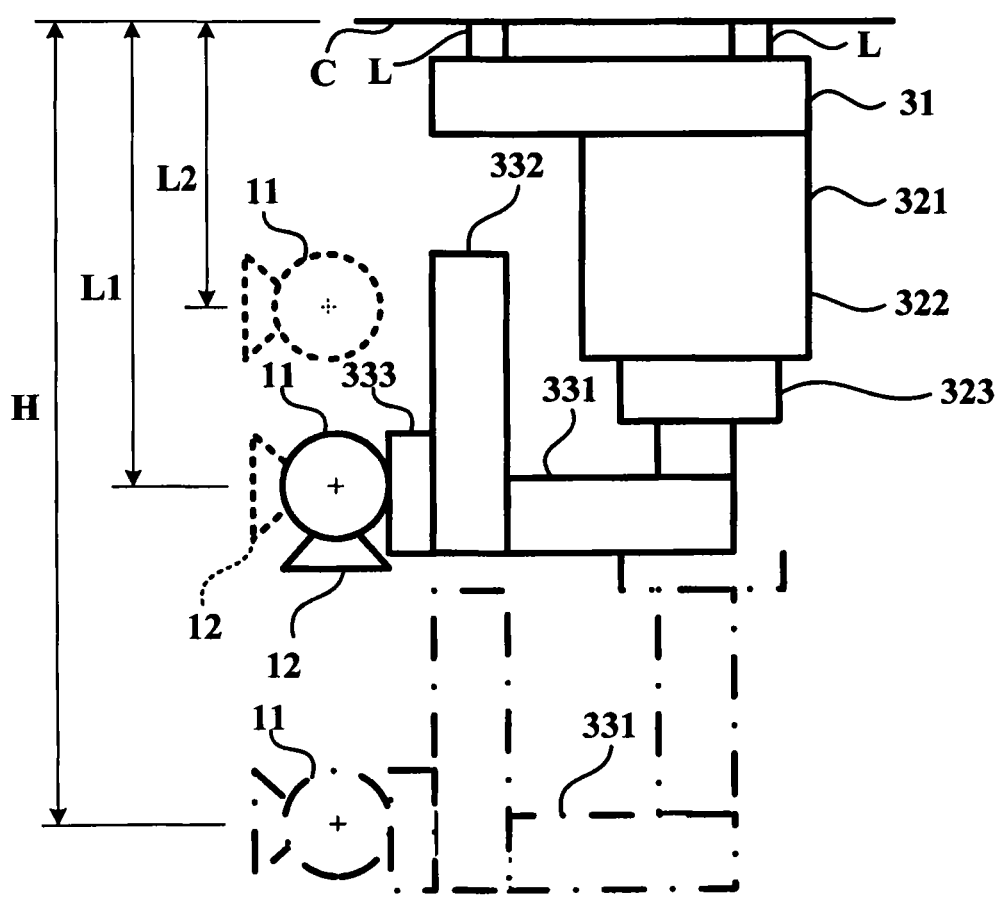
FIG. 8 is a view describing the operation of the pillar section and the height adjuster.

FIGS. 7 and 8 show the supporting member 30 installed in a rail L below the low ceiling C. As shown in FIGS. 7 and 8, the bottom pillar 323 is moved to the higher position by contracting the pillar section 32 to raise the position of the X-ray tube 11 installed on the bottom pillar 323 higher. The X-ray tube 11 is held in the higher position to fit the low ceiling C.

In the operation of the height adjuster 40, the vertical position of the tip section 333 of the arm member 33 and the X-ray tube 11 are raised by rotating the motor 41 clockwise at a predetermined rotation angle. The X-ray tube 11 which is adjusted to the highest position relative to the middle section 332 of the arm member 33 is shown in FIG. 7.

Also, the vertical position of the tip section 333 of the arm member 33 and the X-ray tube 11 are lowered by rotating the motor 41 counterclockwise at a predetermined rotation angle. The X-ray tube 11, which is adjusted to the lowest position relative to the middle section 332 of the arm member 33, is shown in FIG. 6.

When the pillar section 32 and X-ray tube 11 are in the state shown by the long dashed dotted line in FIG. 8, the X-ray tube 11 is located at distance H from the ceiling C. Next, when the pillar section 32 is contracted, the X-ray tube 11 is located at distance L1 from the ceiling C as shown in FIG. 8 in which the X-ray tube 11 is indicated by a solid line. That is, the X-ray tube 11 can be moved within a range (H-L1) by extending and contracting the pillar section 32.

Next, when the X-ray tube 11 shown by the solid line in FIG. 8 is moved further upward by using the height adjuster 40, the X-ray tube 11 is located at distance L2 from the ceiling C (the highest position) (the X-ray tube 11 is shown by a dashed line in FIG. 8). That is, the X-ray tube 11 can be moved within a wide range (H-L2) by extending and contracting the pillar section 32 using the height adjuster 40.

As described above, even if the ceiling C is low, it is possible to address supine full-length radiography in which the subject is lying down while photographing the extensive part of the subject by widening the irradiation field of X-rays by making the position of the X-ray tube 11 sufficiently high using the height adjuster 40 and also contracting the pillar section 32 to adjust the X-ray tube 11 to the highest position (see the position of the X-ray tube 11 shown as a solid line in FIG. 7, and by the dashed line in FIG. 8).

[Variations]

Figure 9:
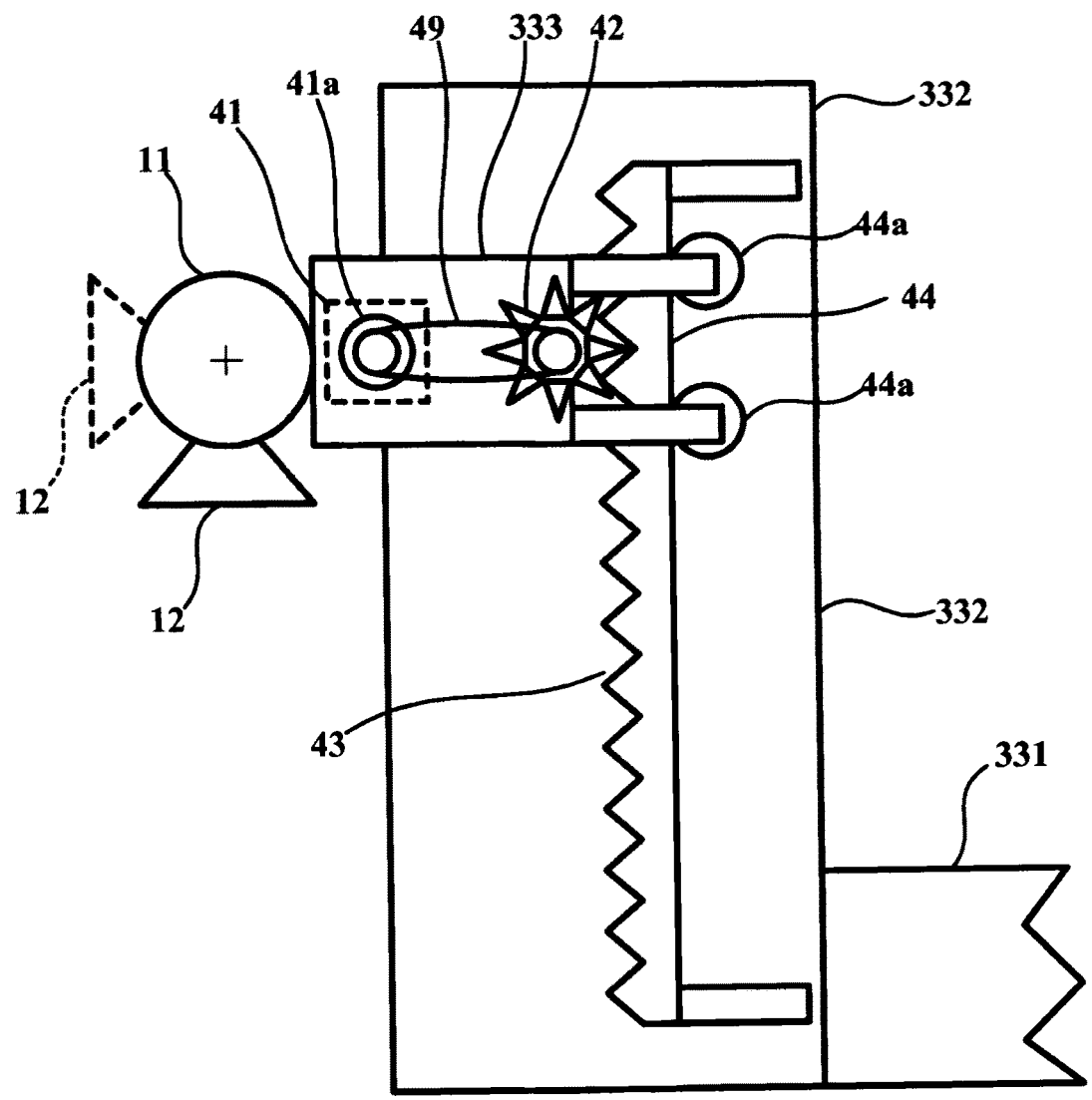
FIG. 9 is a front view of the height adjuster according to the variation.

Next, a variation of the X-ray diagnostic system according to the first embodiment is described with reference to FIG. 9. In this description of the variation, identical numbers are attached to the same configuration as in the first embodiment and so an explanation is omitted.

The configuration of the height adjuster 40 according to the variation is different from the first embodiment in that the position of the rotation axis of the motor 41 and the position of the rotation axis of the pinion 42 are staggered. Thereby, the motor 41 can be provided in the optimal position on the tip section 333 of the arm member 33. A belt 49 for transmitting power from the motor 41 to the pinion 42 is wrapped around the rotation axis of motor 41 and the rotation axis of pinion 42. As an alternative for the belt, a chain can be used.

In addition, although the rack 43 is provided on the middle section 332 side of the arm member 33, and the motor 41 and pinion 42 are provided on the tip section 333 side of the arm member 33 in the first embodiment and its variation, the rack 43 can be provided on the tip section 333 side of the arm member 33 and the motor 41 and pinion 42 can be provided on the middle section 332 side of the arm member 33.

In the X-ray diagnostic system according to the first embodiment, the height of the position of the X-ray tube 11 provided on the tip section 333 is adjusted by vertically moving the tip section 333 of the arm member 33 by extending and contracting the pillar section 32 and by operating the height adjuster 40. Thereby, it is possible to fit the position of the X-ray tube 11 to supine full-length radiography and standing full length radiography of the lower extremities without being affected by the height of the ceiling.

A variation of the first embodiment is described next.

Figure 10:
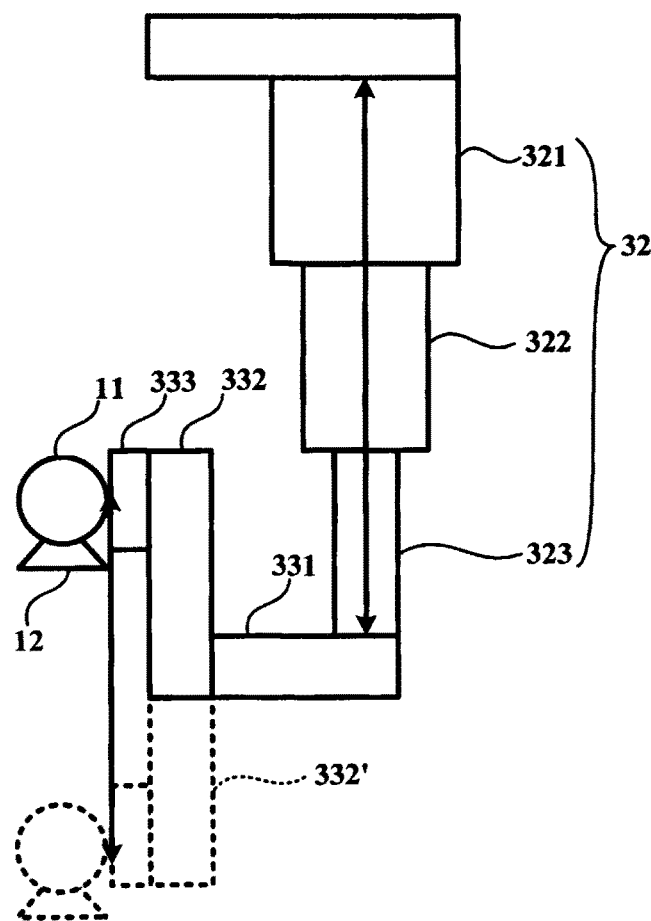
FIG. 10 is a front view illustrating a variation of the first embodiment.

FIG. 10 shows the variation; the middle section 332 is mounted in an erect manner on the base end section 331 of the arm member which is fixed to the bottom pillar 323 of the pillar section 32 and extends horizontally, the tip section 333 is provided vertically movably on this middle section, and the X-ray tube section 11 and diaphragm 12 are mounted on this tip section 333. This configuration is the same as the first embodiment.

This variation is characterized in that the middle section 332 of the arm member is configured to be vertically (shown by an arrow in the figure) movable relative to the base end section 331. The upward position is indicated as 332 and the downward position is indicated as 332'.

Figure 11A:
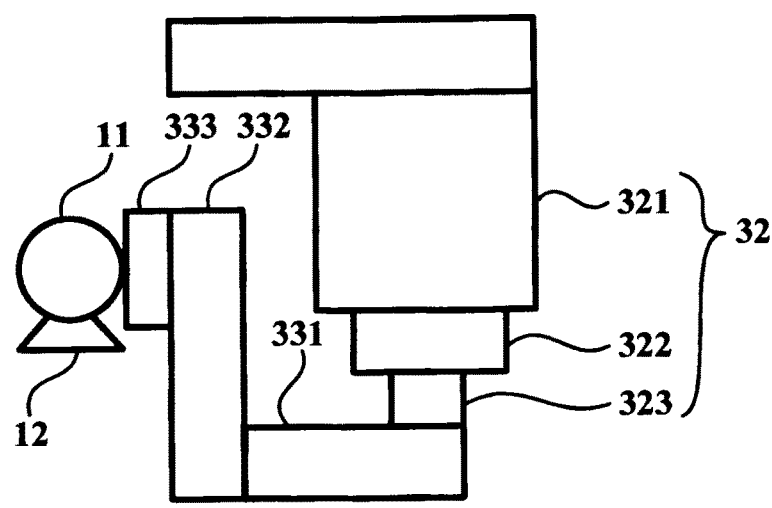
FIG. 11A is a view describing the operation of FIG. 10.
Figure 11B:
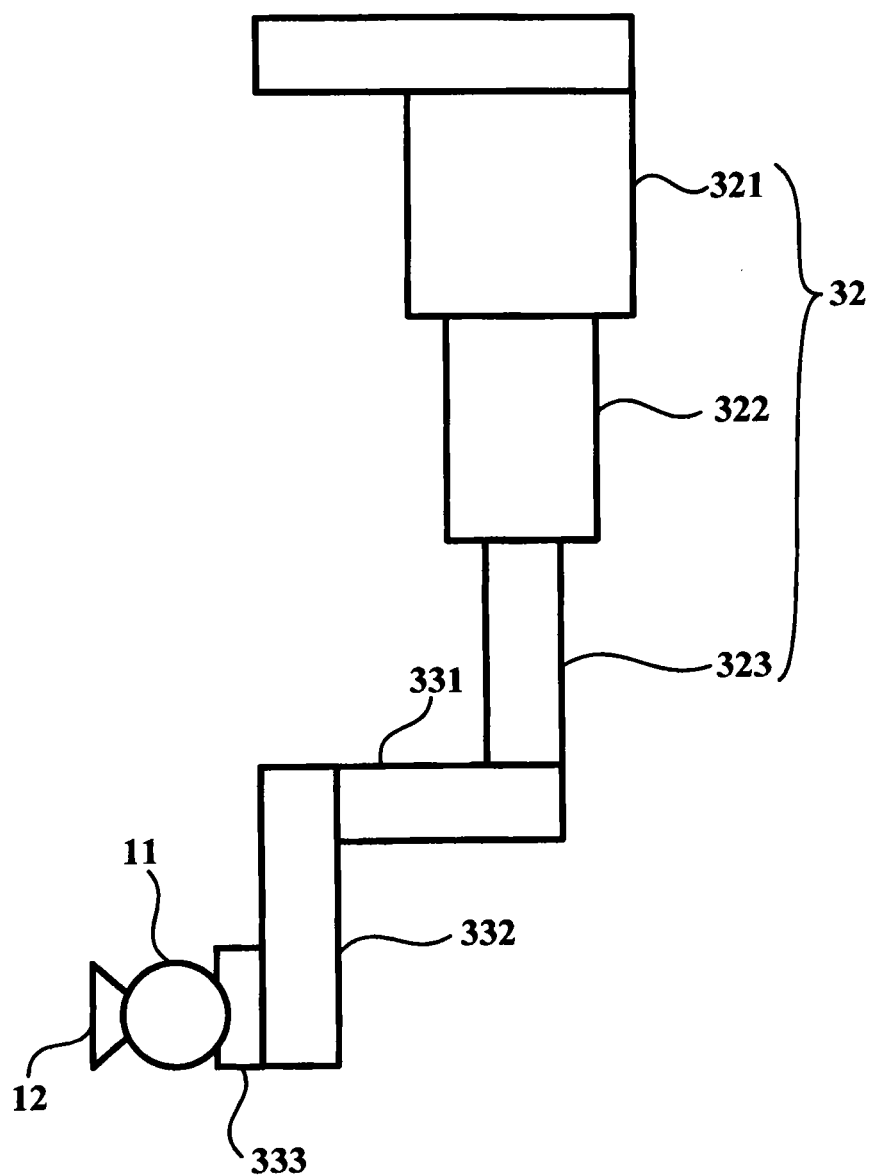
FIG. 11B is a view describing the operation of FIG. 10.

In such a configuration, the X-ray tube 11 and the diaphragm 12 can be positioned as upward as possible, as shown in FIG. 11A, and at the same time, the X-ray tube 11 and the diaphragm 12 can be placed at the lowest downward position as shown in FIG. 11B by moving the middle section 332 of the arm member to a further lower position. When placed at the lowest downward position, the orientation of the X-ray tube 11 and the diaphragm 12 has to be moved horizontally as described in the first embodiment.

Figure 12:
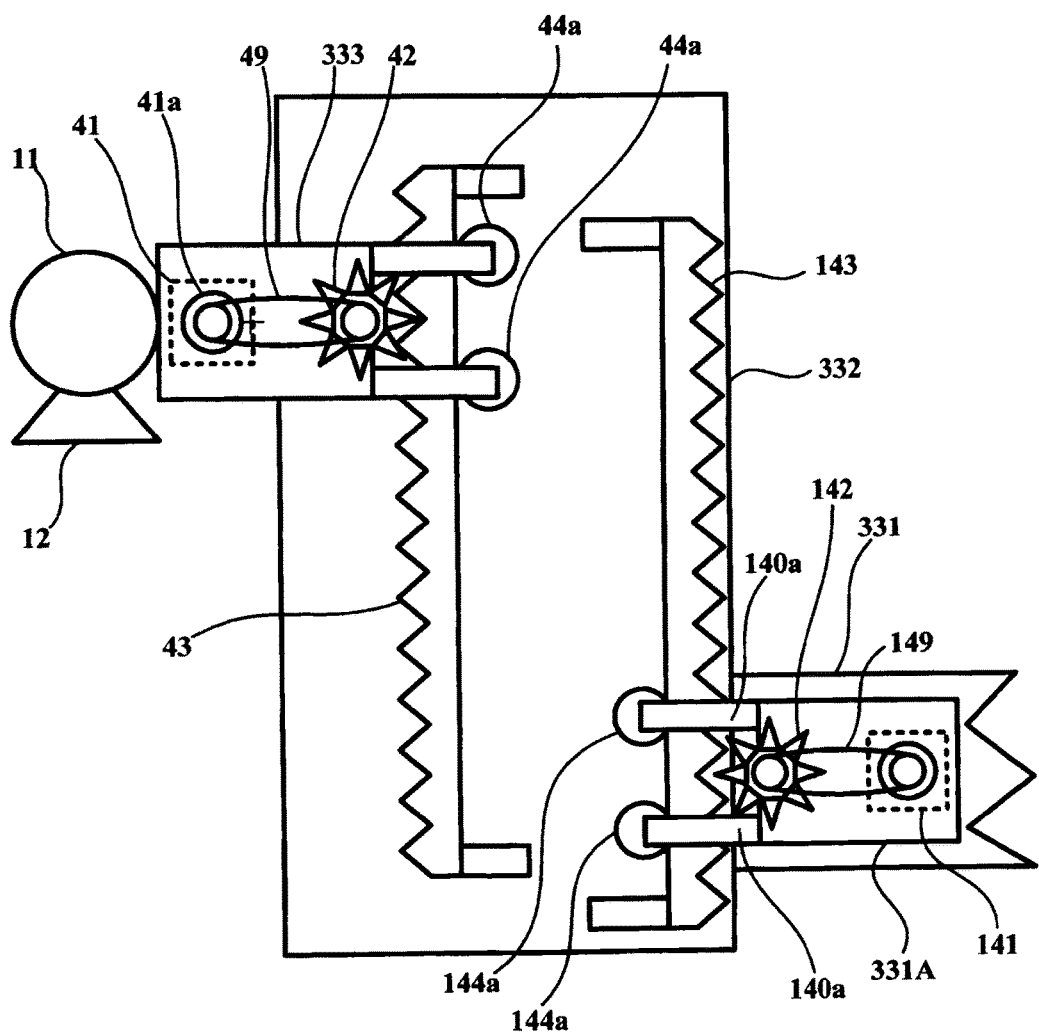
FIG. 12 is a cross-sectional view illustrating the detailed configuration of the apparatus shown in FIG. 10.

FIG. 12 shows a detailed example of the configuration for vertically moving the middle section 332 of the arm member. As shown in the same figure, in addition to the first rack/pinion mechanism consisting of a rack 43 and a pinion 42, the second rack/pinion mechanism is configured by adding a rack 143 on the right hand side, as shown in the figure, of the middle section 332 and by providing a motor 141 and a pinion 142 on the base end section 331 side, so that the middle section 332 can be configured to be vertically movable relative to the base end section 331. The pinion 142 is configured such that the power of motor 141 mounted on the base end section 331 is transmitted via a belt 149, and these pinions 142 and motors 141 are supported by a support box 331A mounted on the base end section 331 on the left hand side, as shown in the figure. Also, this support box 331A is coupled to the roller 144a rolling on the back of the rack 143 via a pair of support pieces 140a and 140a.

By having a configuration as above, the pinion 142 rolls on the surface of the rack 143 in accordance with the rotation of the motor 141 mounted on the support box 331A, the middle section 332 of the arm member vertically moves relative to the base end section 331, and the range of motion is further increased compared to the first embodiment.

Second Embodiment

Figure 13:
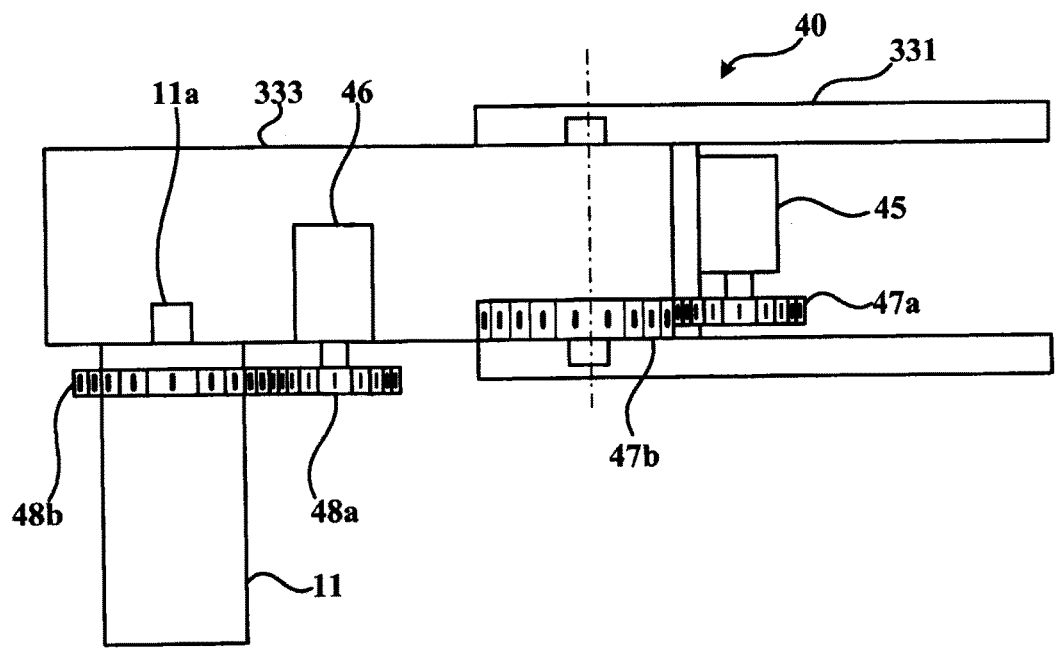
FIG. 13 is a plane view of the height adjuster according to the second embodiment.
Figure 14:
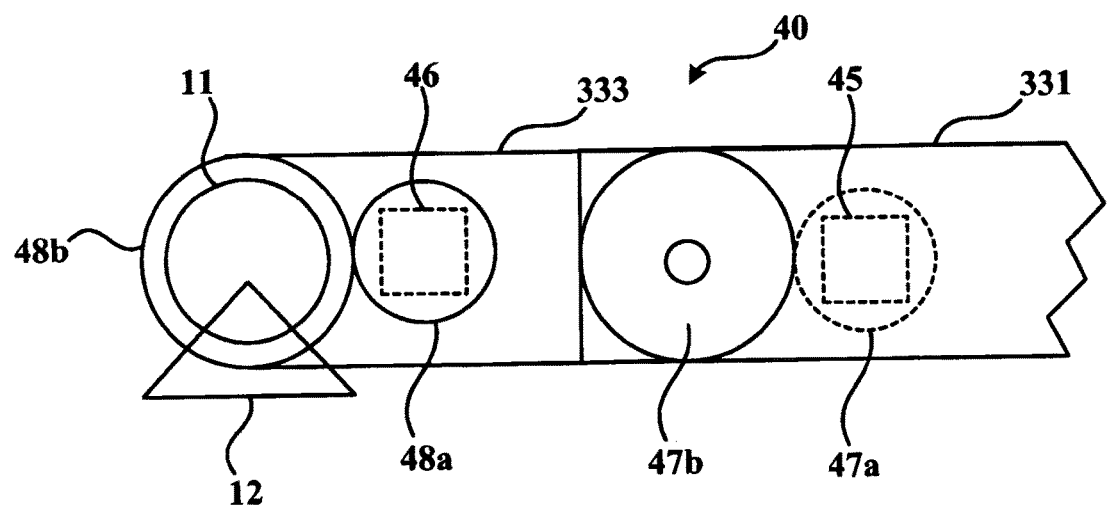
FIG. 14 is a front view of the height adjuster.

An X-ray diagnostic system according to the second embodiment is described with reference to FIGS. 13 to 18. FIG. 13 is a plane view of the height adjuster, while FIG. 14 is a front view of the height adjuster.

[Height Adjuster]

While the height adjuster 40 has a sliding mechanism in the first embodiment, in the second embodiment it is different in that it has a rotation mechanism. In the second embodiment, identical numbers are attached to the same configuration as in the first embodiment and so an explanation is omitted.

The rotation mechanism is a mechanism for rotating the tip section 333 of the arm member 33 about a horizontal axis relative to the base end section 331.

The rotation mechanism comprises a motor 45 provided on the base end section 331 of the arm member 33, a first gear 47a fixed to the output axis of the motor 45, and a second gear 47b formed on the tip section 333 of the arm member 33. The second gear 47b has circumferential teeth formed in the coaxial center of the tip section 333 of the arm member 33. When the first gear 47a is rotated by the motor 45 clockwise in FIG. 14, the tip section 333 of the arm member 33 is rotated counterclockwise. When the first gear 47a is rotated by the motor 45 counterclockwise in FIG. 14, the tip section 333 of the arm member 33 is rotated clockwise.

A servomotor is used as an example of a motor 45. The servomotor rotates the first gear 47a at the rotation amount corresponding to the number of pulses and in the rotation direction corresponding to the pulse width by making the pulse frequency constant and modulating the pulse width.

Upon receiving pulses of a predetermined width, the motor 45 rotates the first gear 47a in the rotation direction corresponding to the pulse width and at the rotation amount corresponding to the number of pulses. Thereby, the tip section 333 of the arm member 33 is tilted, and the X-ray tube 11 is moved to the predetermined vertical position.

[Angle Adjuster]

Next, the angle adjuster for changing the direction of X-ray irradiation is described with reference to FIG. 14.

Suppose that the X-ray tube 11 is fixed to the tip section 333 of the arm member 33, when the tip section 333 of the arm member 33 is tilted by the angle adjuster, the direction of X-ray irradiation is changed accordingly, preventing the desired angle from being obtained, which is why the angle adjuster is provided.

The angle adjuster comprises a support axis 11a for supporting the X-ray tube 11 at the tip section 333 of the arm member 33 for rotation; a motor 46 provided on the tip section 333; a third gear 48a fixed to the output axis of the motor 46; and a fourth gear 48b engaged with the third gear 48a and fixed to the X-ray tube 11. When the motor 46 is rotated in the forward or reverse direction as a result of the operation of the operating section (not shown), the third gear 48a and the fourth gear 48b are rotated, and the X-ray tube 11 is rotated one or more times (360 degrees) about the support axis 11a. Thereby, the irradiation direction of the X-ray tube 11 can be changed in response to the position of the photographed object.

[Operation]

Figure 15:
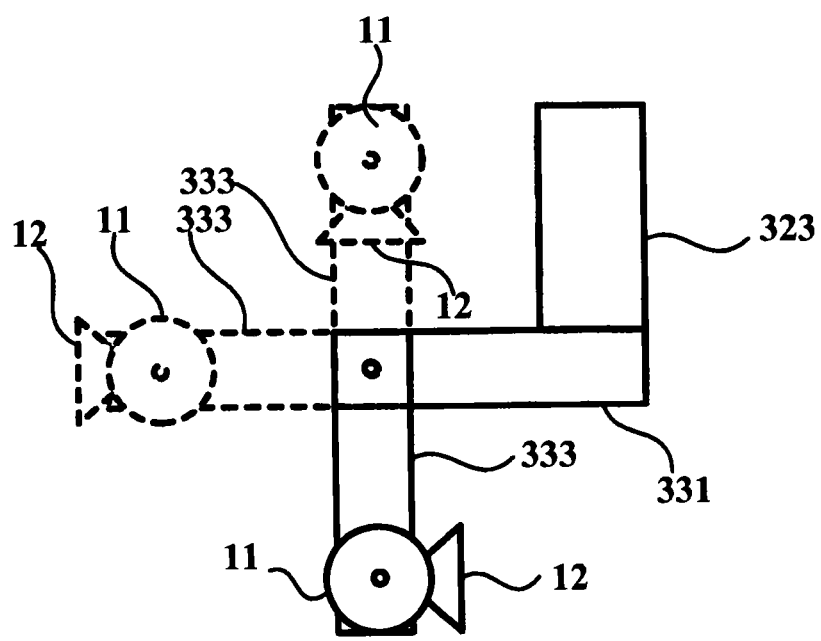
FIG. 15 is a view describing the operation of the height adjuster.

Next, the operation when adjusting the vertical position of the X-ray tube 11 is described with reference to FIG. 15. FIG. 15 is a view describing the operation of the height adjuster 40. In addition to the description of the operation of the height adjuster 40, the operation of the angle adjuster for changing the direction of X-ray irradiation is also described.

As shown in FIG. 15, the height adjuster 40 tilts the tip section 333 of the arm member 33 to each angle of: 0 degrees, 90 degrees clockwise, and 90 degrees counterclockwise (−90 degrees) relative to the base end section 331. When the height adjuster 40 tilts the tip section 333 to the angle of 0 to 90 degrees relative to the base end section 331, the angle adjuster changes the direction of X-ray irradiation to the angle of 180 degrees counterclockwise (−180 degrees) relative to the tip section 333. When the height adjuster 40 tilts the tip section 333 to the angle of 0 to −90 degrees relative to the base end section 331, the angle adjuster changes the direction of X-ray irradiation to the angle of 90 degrees counterclockwise)(−90° relative to the tip section 333.

Figure 16:
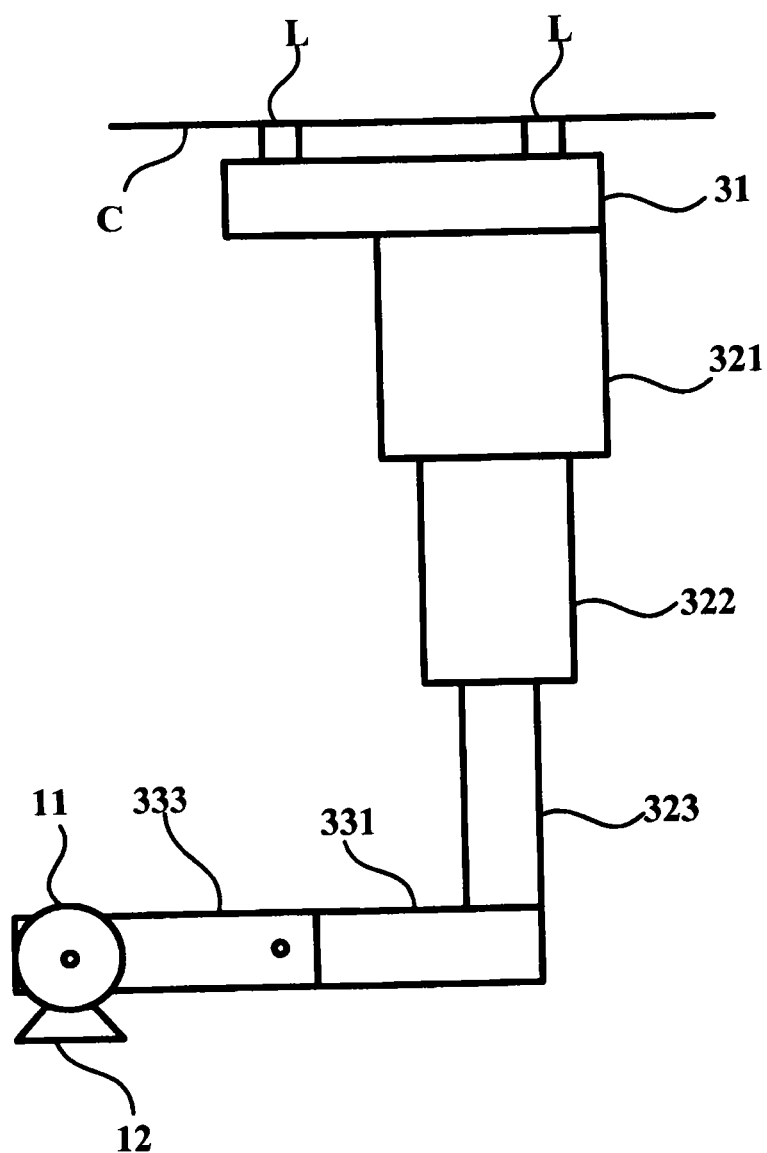
FIG. 16 is a view describing the operation of the pillar section and the height adjuster.
Figure 17:
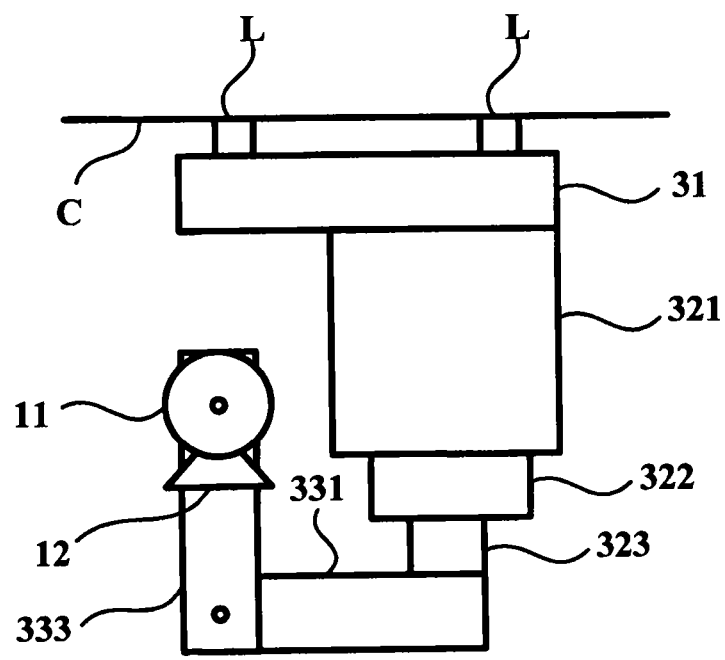
FIG. 17 is a view describing the operation of the pillar section and the height adjuster.
Figure 18:
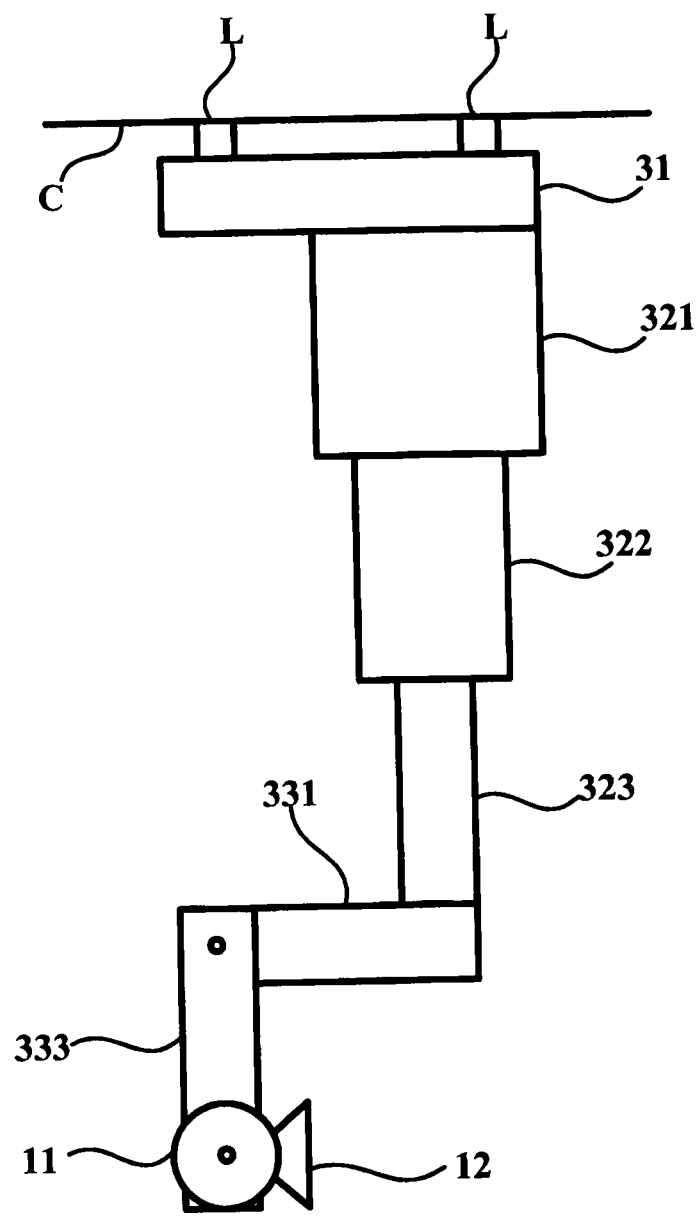
FIG. 18 is a view describing the operation of the pillar section and the height adjuster.
Figure 19:
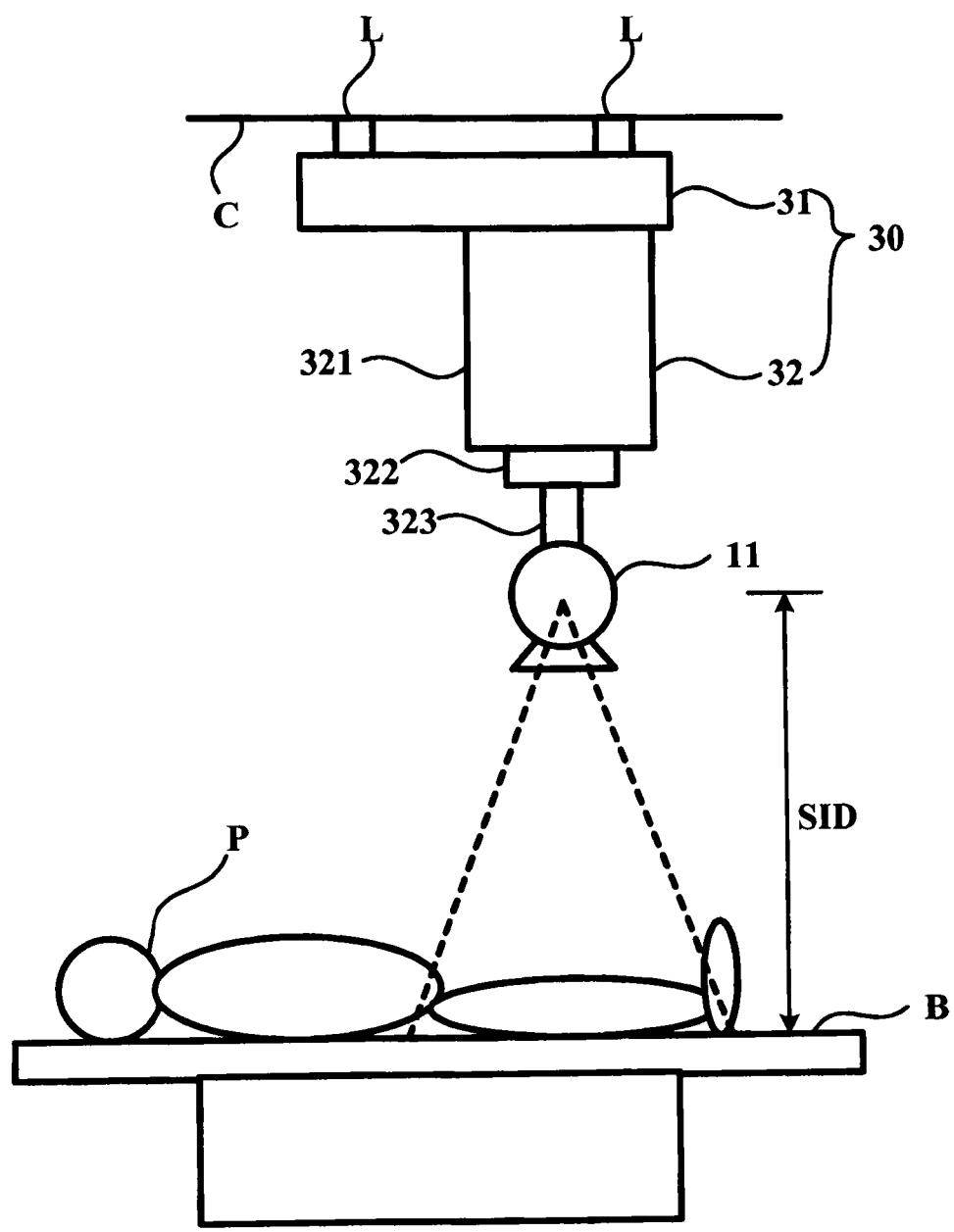
FIG. 19 is an overall view of the X-ray diagnostic system according to the conventional technique.

Next, the operation of the pillar section 32 and the height adjuster 40 is described with reference to FIGS. 16 to 18. FIGS. 16 to 18 are views representing the status of the pillar section 32 and the arm member 33.

As shown in FIG. 16, the pillar section 32 is extended. The height adjuster 40 tilts the tip section 333 of the arm member 33 to the angle of 0 degrees relative to the base end section 331. In addition, the angle adjuster changes the direction of X-ray irradiation to the angle of 90 degrees counterclockwise (−90 degrees) relative to the tip section 333.

In the state shown in FIG. 16, for example, the pillar section 32 is contracted, the height adjuster 40 tilts the tip section 333 of the arm member 33 to the angle of 90 degrees clockwise relative to the base end section 331, and the angle adjuster changes the direction of X-ray irradiation to the angle of 90 degrees counterclockwise (−90 degrees) relative to the tip section 333 (see FIG. 17). Thereby, the X-ray tube 11 is adjusted to the higher position, the irradiation range of X-ray is widened, and supine full-length radiography can be performed while the subject is lying on a bed.

In the state shown in FIG. 16, the pillar section 32 remains extended, for example. The height adjuster 40 tilts the tip section 333 of the arm member 33 to the angle of 90 degrees counterclockwise (−90 degrees) relative to the base end section 331, and the angle adjuster does not change the direction of X-ray irradiation relative to the tip section 333 (see FIG. 18). Thereby, the position of the X-ray tube 11 becomes sufficiently low, allowing the subject's heel to be photographed while the subject is standing (standing full length radiography of the lower extremities).

In the X-ray diagnostic system according to the second embodiment, by extending and contracting the pillar section 32 and operating the height adjuster 40, the tip section 333 of the arm member 33 is tilted relative to the base end section 331 such that the position of the X-ray tube 11 provided on the tip section 333 can be adjusted. Thereby, it is possible to fit the position of the X-ray tube 11 to supine full-length radiography and standing full length radiography of the lower extremities without being affected by the height of the ceiling C.

Other Embodiments

Figure 20:
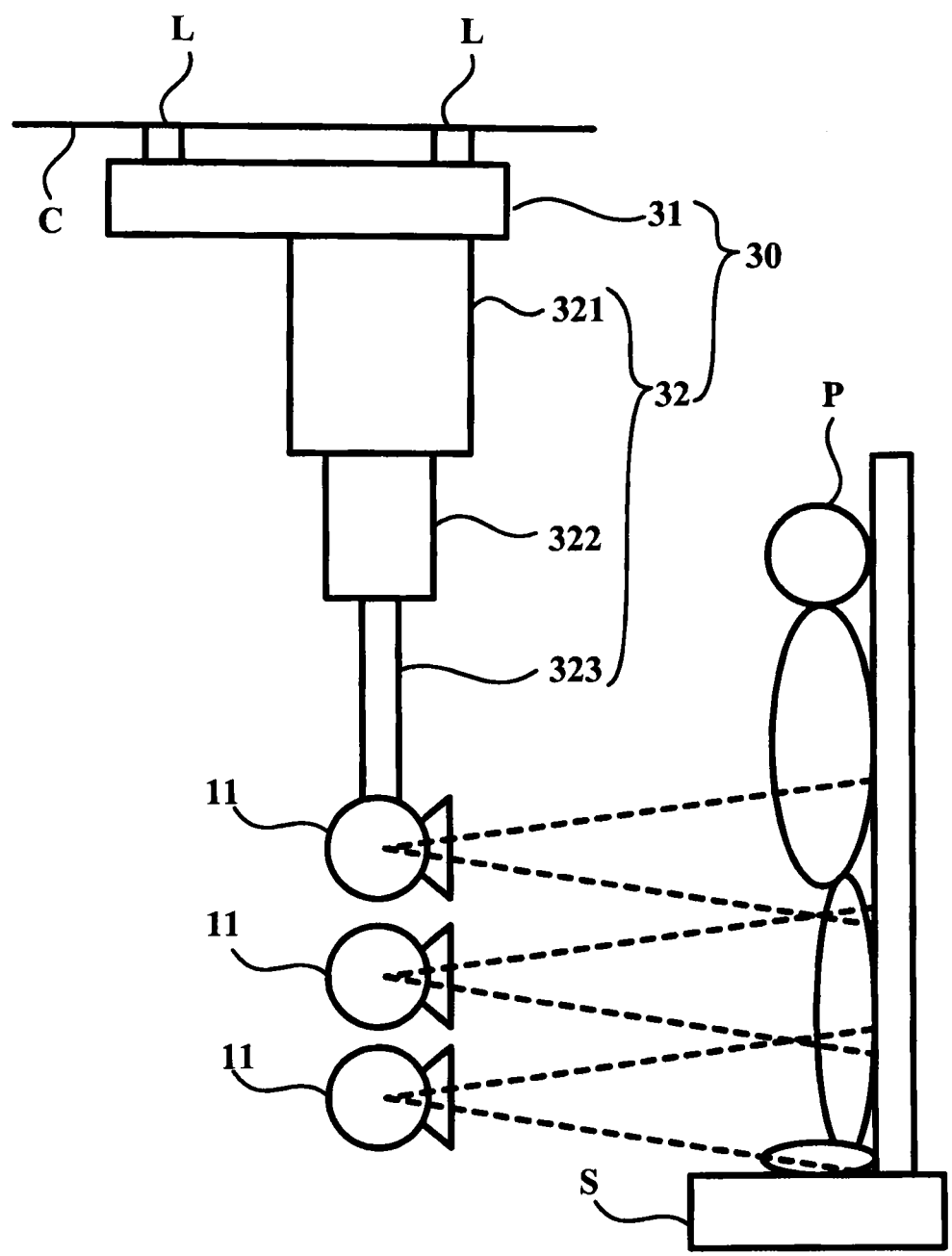
FIG. 20 is an overall view of the X-ray diagnostic system according to the conventional technique.
Figure 21:
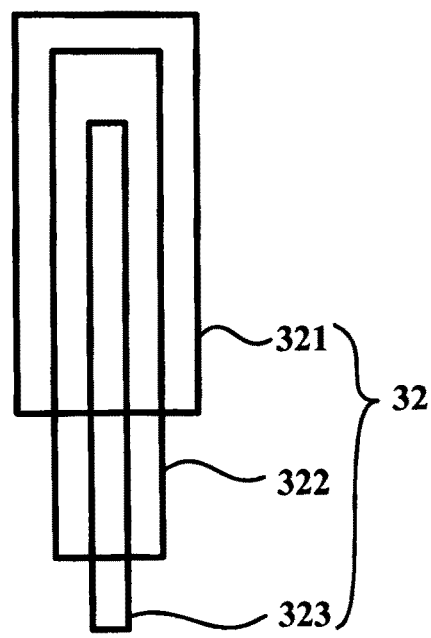
FIG. 21 is an explanatory drawing of the supporting member when each pillar is elongated.
Figure 22:
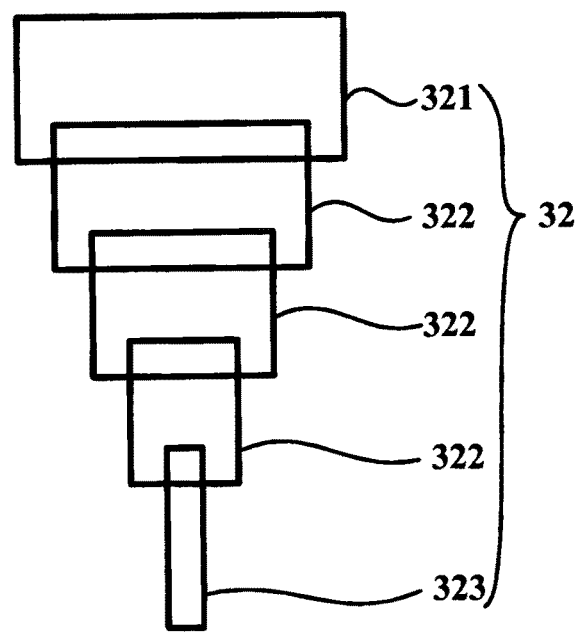
FIG. 22 is an explanatory drawing of a supporting member having multiple pillars.
Figure 23:
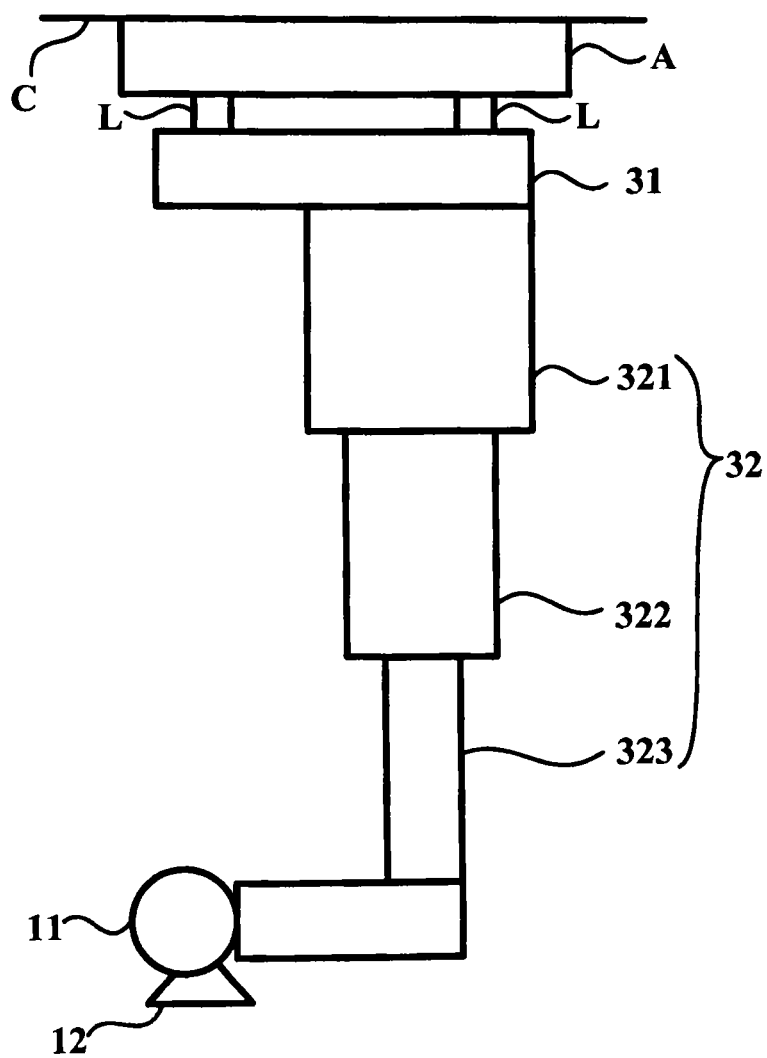
FIG. 23 is an overall view of the X-ray diagnostic system according to the conventional technique.
Figure 24:
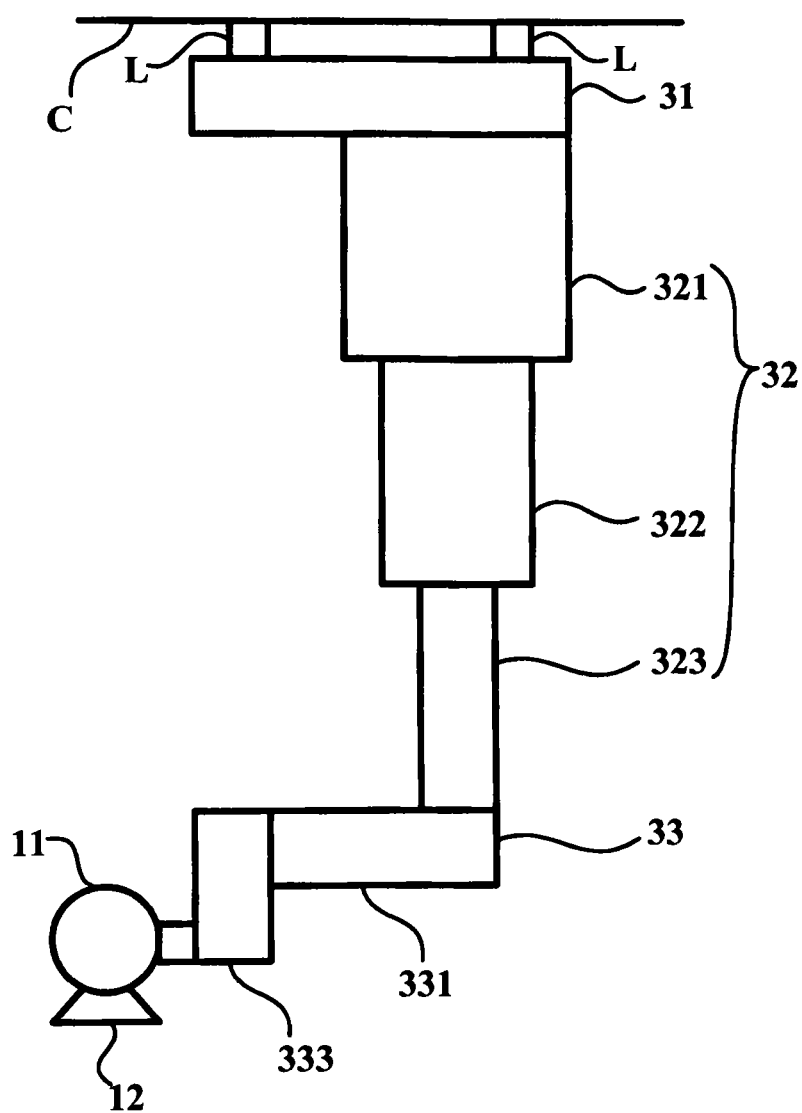
FIG. 24 is an overall view of the X-ray diagnostic system according to the conventional technique.
Figure 25:
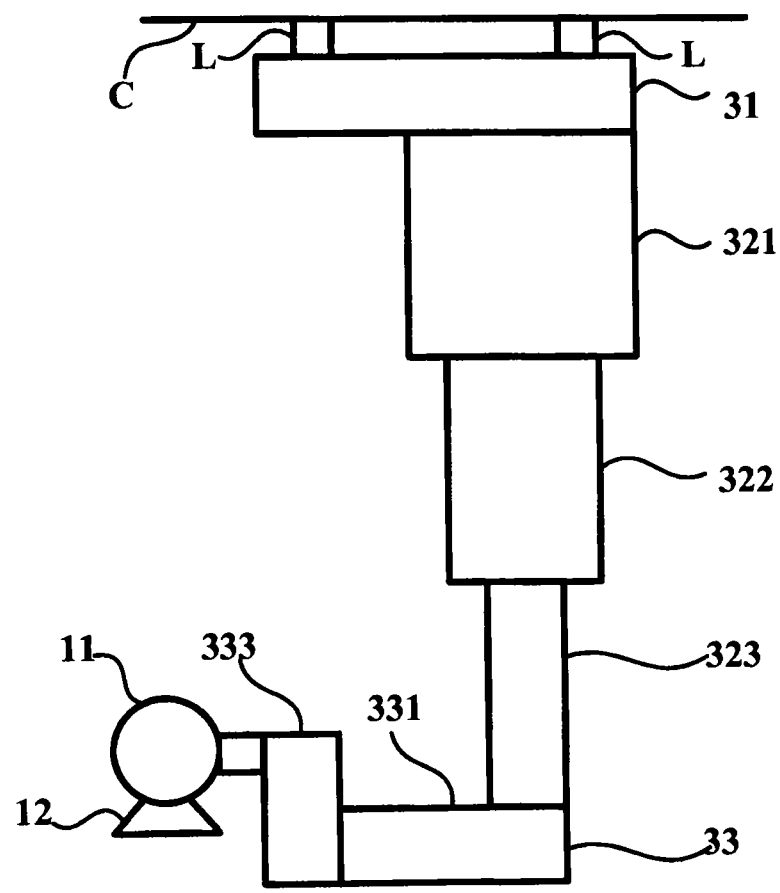
FIG. 25 is a view illustrating the inverted arm member attached to the supporting member.

In contrast to the conventional X-ray diagnostic system as shown in FIG. 20, the height of the position of the X-ray tube 11 can be adjusted in the same way as in the X-ray diagnostic system according to the embodiment by providing the arm member 33 and the height adjuster 40, and vertically moving the tip section 333 of the arm member 33 with the height adjuster 40. In addition, since the arm member 33 and the height adjuster 40 are provided, thereby increasing the weight, it is necessary to balance the weight of the extension/contraction mechanism, for example, by adjusting the force to retain each pillar of the pillar section 32 in their predetermined positions.

The height adjuster 40 according to the first embodiment can be combined with the height adjuster 40 according to the second embodiment. It is possible to move the X-ray tube 11 further upward by the height adjuster 40 according to the first embodiment after the X-ray tube 11 is raised to the highest position by the height adjuster 40 according to the second embodiment. It is also possible to move the X-ray tube 11 further downward by the height adjuster 40 according to the first embodiment after the X-ray tube 11 is lowered to the lowest position by the height adjuster 40 according to the second embodiment. That is, the height adjusting range of the position of the X-ray tube 11 can be enlarged by having two types of height adjusters 40 operate.

In addition, in the embodiments, the operating section 19 was provided on the console panel in the operation room. Additionally, the operating section 19 can be provided in or adjacent to the height adjuster 40. Since an operator can operate the operating section 19 near the X-ray tube 11 and the subject, the operability in adjusting the height of the position of the X-ray tube 11 can be improved.

Furthermore, although the height adjuster 40 for adjusting the height of the position of X-ray tube 11 and the angle adjuster for changing the angle of the direction of X-ray irradiation are operated separately in the embodiments, the height adjuster 40 and the angle adjuster can be coordinated. For example, they can be coordinated to tilt the angle of the tip section 333 of the arm member 33, while maintaining the direction of X-ray irradiation in a constant direction (downward or horizontal direction).

Moreover, in the embodiments, although the height adjuster 40 vertically moving the X-ray tube 11 by the power of the motor 41 is shown, it could be a height adjuster 40 for vertically moving the X-ray tube 11 by the manual operation of an operator, etc. Also, although the angle adjuster for adjusting the direction of X-ray irradiation by the power of the motor 46 is shown in the embodiments, it could be an angle adjuster for adjusting the direction of X-ray irradiation by a manual operation of an operator, etc.

Also, in the embodiments, the rail L below the ceiling C of the room is used as an example of the installation of the supporting member 30; however, as long as it is a place or position in the part of the room where the supporting member 30 can be installed in a state of being suspended, an adaptor, etc. can be added or the rail L can be removed.

While some embodiments of the invention have been described, these embodiments are presented as examples and are not intended to limit the scope of the invention. These novel embodiments can be conducted in other various forms, and various omissions, re-writings, and alterations may be carried out without departing from the spirit of the invention. These embodiments and their variations are included in the scope and spirit of the invention, and also included in the scope of the invention described in the claims and its equivalent.

EXPLANATION OF THE SYMBOLS

A adaptor
B bed
C ceiling
L rail
P subject
S platform for photography
11 X-ray tube
12 diaphragm
13 X-ray detecting section
14 grid
15 X ray high-voltage unit
16 high-voltage generator
17 X-ray controller
18 hand switch
19 operating section
20 image processing unit
21 controller
22 control signal input-output section
23 image input section
24 input-output section
24a external memory
24b keyboard
24c mouse
25 memory
26 image processing section
27 display output section
28 monitor
29 network input-output section
30 supporting member
31 base section
32 pillar section
321 upper pillar
322 middle pillar
323 bottom pillar (the lower end portion of the supporting member)
33 arm member
331 base end section 332 middle section
333 tip section
40 height adjuster
41 motor
42 pinion
43 rack
44 guiderail
44a roller
45 motor
46 motor
47a first gear
47b second gear
48a third gear
48b fourth gear
49 belt
50 drive controller
51 controller
52 power supply section
53 detected signal input section
54 input section

The invention claimed is:

1. An X-ray diagnostic system that obtains images based on detection of X-rays transmitted through a subject, comprising:

a supporting member including a base fixed to a ceiling, and a pillar mounted on the base, the pillar configured to be vertically expandable and contractible;

an arm member having a base end section fixed to a lower end portion of the pillar to extend horizontally, a middle section provided to the base end section and configured to be movable along the pillar to positions above and below the lower end portion of the pillar, and a tip section provided to the middle section and configured to be movable up and down along the middle section; and an X-ray tube arranged on the tip section.

2. The X-ray diagnostic system according to claim 1, further comprising a first sliding mechanism configured to vertically move the tip section with respect to the middle section.

3. The X-ray diagnostic system according to claim 2, further comprising a second sliding mechanism configured to vertically move the tip section with respect to the base end section.

* * * * *